| United States Patent [19] | [11] Patent Number: 4,874,738 |
| Brazdil, Jr. et al. | [45] Date of Patent: Oct. 17, 1989 |

[54] CATALYST FOR AMMOXIDATION OF PARAFFINS

[75] Inventors: James F. Brazdil, Jr., Mayfield Village; Linda C. Glaeser, Lyndhurst; Mark A. Toft, Lakewood, all of Ohio

[73] Assignee: The Standard Oil Company, Cleveland, Ohio

[21] Appl. No.: 242,236

[22] Filed: Sep. 9, 1988

[51] Int. Cl.[4] .................... B01J 27/16; B01J 27/18; B01J 27/188; B01J 27/198
[52] U.S. Cl. .................................... 502/209; 502/204; 558/319
[58] Field of Search ................ 502/204, 209; 558/319

[56] References Cited

U.S. PATENT DOCUMENTS

| 3,433,823 | 3/1969 | McMahon | 502/204 X |
| 4,166,190 | 8/1979 | White et al. | 502/209 X |
| 4,563,439 | 1/1986 | Bremer et al. | 502/209 |
| 4,788,173 | 11/1988 | Glaeser et al. | 502/209 X |

*Primary Examiner*—W. J. Shine
*Attorney, Agent, or Firm*—C. S. Lynch; D. J. Untener; L. W. Evans

[57] ABSTRACT

Disclosed is the reaction of propane and isobutane with $O_2$ and $NH_3$ to make $\alpha,\beta$-unsaturated nitriles and olefins, using certain complex metal oxide catalyst compositions and an excess of the paraffin over both the $O_2$ and the $NH_3$. Also disclosed are suitable catalyst compositions for such reactions.

4 Claims, No Drawings

CATALYST FOR AMMOXIDATION OF PARAFFINS

This invention relates to the catalytic ammoxidation of propane and isobutane to α,β-unsaturated mononitriles; i.e., acrylonitrile and methacrylonitrile, and to catalyst compositions for such ammoxidation.

Because of the price differential between propylene and propane an economic incentive exists for the development of a viable catalytic process for conversion of propane to acrylonitrile.

In U.S. Pat. No. 3,433,823 is disclosed a process for reacting paraffins such as isobutane with oxygen and ammonia to make methacrylonitrile using a mixture of a first catalyst and a second catalyst. The first catalyst can be a vanadium phosphate and the second an oxide of Mo, Cu, W, Th, V or Zr. It is not disclosed, however, to use an excess ratio of isobutane to $O_2$. In the actual examples using isobutane as the substrate, a large excess of oxygen is used and the results are poor.

In Chemical Abstracts, Vol. 88:90239d is disclosed the reaction of propane with $NH_3$ and $O_2$ using excess $NH_3$ and excess $O_2$ and an oxide catalyst containing only V, P and O. Only 40.5 percent of the propane was converted, and only 29.4 percent of propane fed was converted to acrylonitrile.

An article in Applied Catalysis, 33 (1987) by Centi et al, on pages 343–359 discusses, inter alia, the ammoxidation of propane with very large excesses, which are totally uneconomical, of oxygen and ammonia over that required to stoichiometrically ammoxidize propane. The results are also very poor. The catalyst is $(VO)_2P_2O_7$.

It is an object of the present invention to provide an improved process for the ammoxidation of paraffins to unsaturated mononitriles and the corresponding monoolefins.

It is a further object of the invention to provide new catalysts for such reaction.

Still another object is to provide an improved catalytic ammoxidation process for making certain unsaturated mononitriles and olefins (propylene and isobutylene) from lower paraffins without the use of halogen promoters.

Other objects, as well as aspects, features and advantages, of the present invention will become apparent from a study of the accompanying disclosure and the claims.

These and other objects are achieved by the present invention according to one aspect of which there is provided a process for making an α,β-unsaturated mononitrile by the catalytic reaction of a paraffin selected from propane and isobutane with oxygen and ammonia by catalytic contact of the foregoing reactants in a reaction zone with a complex metal oxide catalyst composition that has 0–99 weight percent of a diluent/support and 100–1 weight percent of a catalyst having the elements and the proportions indicated by the empirical formula:

$$VP_pW_wA_aD_dC_cT_tO_x \qquad \text{(formula 1)}$$

where
A is one or more of Sn, Mo, B and Ge;
D is one or more of Fe, Co, Ni, Cr, Pb, Mn, Zn, Se, Te, Ga, Zr, In and As;
C is one or more of an alkali metal and Tl;
T is one or more of Ca, Sr, Mg and Ba; and
where
a is 0–10; d is 0–10; c is 0–1; t is 0–10; p is 0.1–20; w is 0.2–10; the ratio $(a+c+d+t+w):(1+p)$ is no more than 6; and no more than 2 atoms of Mo are present per atom of V; the reactants fed to the reaction zone containing a mole ratio of paraffin:$NH_3$ in the range from 2 to 16 and a mole ratio of paraffin to $O_2$ in the range from 1 to 10.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the alkane feed to the process can contain one or more $C_3$ to $C_4$ olefins. The $C_3$ to $C_4$ olefin content of the feed to the present ammoxidation process can contain from zero to 8 mole percent of such olefin(s), based on the moles of $C_3$ to $C_4$ paraffins plus olefins fed, and this feed can be from any source. Although larger amounts of $C_3$ to $C_4$ olefins may be present in the substrate paraffin feed, usual amounts are as stated, and the usual olefin is that corresponding to the particular paraffin fed to the reaction zone of the present process.

The nitrile products of the present process contain one C to C double bond and one nitrile group. The desired olefin products contain one double bond and the same number of C atoms as the paraffin feed.

The above catalysts usually include at least 0.4 atom of W per atom of V. Particularly useful are catalysts containing at least 0.5 atoms of P per atom of V.

Vanadium, phosphorus, tungsten and the optional elements shown in the catalyst formula 1 can be incorporated by methods generally known in the art, using oxides, hydroxides, acids, salts (particularly organic salts such as acetates), and other compounds of such elements. Examples of such incorporation are shown in the specific examples hereinafter.

Tungsten is advantageously incorporated as ammonium meta- or orthotungstate, tungstic acid, or tungsten trioxide. P can be introduced, for instance, as ammonium phosphate or $(NH_4)_2HPO_4$ or phosphoric acid.

The catalysts of formula 1 can, of course, contain oxides of other elements not set forth in formula 1, as long as they do not materially detrimentally affect the catalytic ammoxidation of the paraffin to the desired nitriles. When bismuth is optionally present in oxidized form as part of the catalyst of formula 1, it is usually present in amounts of no more than 0.2 atoms of Bi per atom of V. Usually, catalysts of formula 1 contain essentially no antimony but in any event they never contain more than 0.01 atom of Sb per atom of V.

In the process of the present invention, the reaction is preferably carried out in the gas phase by contacting a mixture of the paraffin, ammonia and a molecular oxygen containing gas, such as air, with a catalyst of the invention contained in a fixed bed, a gravity flowing bed, a fluidized bed or a fast transport reactor mode. It is also possible to include additional diluents such as steam, nitrogen, carbon dioxide or helium.

It should be noted that when operating at ratios of paraffin to oxygen and to ammonia in excess of stoichiometric, as in the present process, 100 percent conversion of paraffin is not even theoretically attainable. However, when so operating, an advantage is that the selectivity of the paraffin to the corresponding nitrile and the corresponding olefin is greatly increased, and the olefin product can be further ammoxidized with $O_2$ and $NH_3$ to make further quantities of the nitrile. Thus, the nitrile and the corresponding olefin are both useful products of the present process. The unreacted olefin and paraffin can, of course, be fed to an ammoxidation step or steps.

The reaction temperature can vary from 400° to 650° C., but is usually 460° to 520° C. The latter temperature ranges are especially useful in the case of propane ammoxidation to acrylonitrile.

The average contact time is usually from 0.02 to 20 seconds, and is more often from 0.2 to 8 seconds, but higher or lower contact times can be used.

The catalysts of formula 1 of the present invention, and used in the process of the invention, are essentially free of uranium. Moreover, in the process of the invention, essentially no sulfur or sulfur compounds, or halogen or halogen compounds, are present in the reaction mixture during the ammoxidation.

In the process of the present invention, the complex metal oxide catalyst composition of the foregoing formula 1 can be in a physical admixture with a particular co-catalyst. This results in an increase in the selectivity of alkane conversion to the mononitrile.

Thus, according to this aspect of the invention, the process for making an $\alpha,\beta$-unsaturated nitrile recited hereinbefore is effected while said catalyst is in particulate form admixed with a co-catalyst composition also in particulate form and having 0-99 weight percent of a diluent/support and 100-1 weight percent of a co-catalyst having the elements and the proportions indicated by the empirical formula:

   (formula 2)

where

D is one or more of Fe, Mn, Pb, Co, Ni, Cu, Sn, P, Cr, Y, Mg, Ca, Sr, Ba and rare earths other than Ce and Sm E is one or more of Sb, Ge, As, Se, Te and V F is one or more of an alkali metal, Tl, Ag and Sm and where n is 0.01-24, p is 0.01-24, (n+p) is 0.1-24, d is 0-10, e is 0-10, f is 0-6, g is 0-8, y is determined by the oxidation state of other elements, wherein the weight ratio in said mixture of said catalyst composition to said co-catalyst composition is in the range of 0.001 to 2.5.

In the present process in all its embodiments the molar ratio of $O_2$ to $NH_3$ fed to the reaction zone is usually in the range from 1 to 10 (more often 1-5) and the molar ratio of gaseous diluent to alkane or paraffin is usually in the range of zero to 5 (more often zero to 3).

In the preparation of the co-catalyst composition of formula 2, the metal oxides can be blended together or can be formed separately and then blended or formed separately or together in situ. Promoter oxides can be incorporated into the bismuth-cerium-molybdenum based catalyst by blending into the gel before calcining or by blending into the oven-dried base catalyst before calcining. A useful manner of incorporating promoter elements is by choosing a water-soluble salt of the promoter element, forming an aqueous solution of the salt, and mixing the solution with a solution or a suspension of the base elements or salts thereof. Optionally, the promoter elements can be incorporated by the use of soluble complex salts or compounds with the desired base elements which upon calcination will yield the desired ratio of the elements in the finished catalyst.

The F elements can be introduced into the co-catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one can use any compound of iron which, upon calcination, will result in the oxides. As with the other elements, water soluble salts are preferred for the ease with which they may be uniformly dispersed within the catalyst. Most preferred is ferric nitrate. Cobalt and nickel are similarly introduced.

To introduce the molybdenum component any molybdenum oxide such as the dioxide, trioxide, pentoxide or sesquioxide can be used. A preferred starting material is ammonium heptamolybdate.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxide.

These co-catalyst compositions are conveniently prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

In another aspect, the invention concerns the catalyst composition recited hereinbefore, per se. And in still another aspect the invention concerns the admixture of the particulate catalyst composition and the particulate co-catalyst composition per se.

The process of the present invention gives superior results because of the combination of (1) the use of the claimed catalysts at (2) high ratios of alkane feed in relation to $NH_3$ and molecular oxygen, well in excess of the stoichiometric ratio at which all of the alkane could theoretically be converted to the corresponding mononitrile.

The optional diluent/supports for the formula 1 catalysts and for the formula 2 co-catalyst can include alumina, silica-alumina, silica, titania, silica-titania, $Nb_2O_5$, silica-niobia, silica-zirconia, zirconia, etc.

In the usual practice of the present invention, the catalyst support/diluent for the catalyst of formula 1 is not an oxide of an element named in formula 1. Further, in the usual practice of the invention the catalyst support/diluent for the co-catalyst of formula 2 is not an oxide of an element named in formula 2.

In the catalysts of the invention, the empirical formulas 1 and 2 do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times be present as a complex oxide with one, more than one, or all of the elements in formula 1 or formula 2, which complex oxides form during the precipitation or agglomeration, drying and calcining process for preparing the catalyst composition.

In the present application, "rare earths" means elements 57 through 71.

By "particulate mixture" as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

The mixtures of the present catalyst composition and co-catalyst compositions are mixtures of catalysts, not of catalyst precursors. Thus, they are mixtures of catalyst compositions that have been calcined (i.e., heat-treated at the final temperature used for the catalyst preparation).

While particulate catalytic mixtures of formula 1 and formula 2 catalyst compositions are physical mixtures of separate particles of each catalyst composition, pellets or other shapes can be pressed from such particulate mixture to form larger particles for fixed bed operations, etc.

A. N. Shatalova et al. in Neftekhiniya 8, No. 4, 609-612 (1968), describe the reaction of propane with oxygen and ammonia using a large excess of propane and a mixture of two catalysts, one of which is described as oxides of metals having dehydrogenating characteristics, at 550° and 600° C. At 500° C. little or no acrylonitrile was produced. Rather large amounts of propionitrile and acrolein were made per mole of acrylonitrile produced. The per pass conversion of propane to acrylonitrile was generally 2-4 percent with selectivity to acrylonitrile being from 12 to 33 percent.

In copending application Ser. No. 50,268, filed May 15, 1987 by the present inventors is disclosed the ammoxidation of $C_3$ to $C_5$ paraffins, including propane and isobutane to make nitriles, including acrylonitrile and methacrylonitrile, in the presence of a mixture of (1) an oxidic V and Sb-containing catalyst that can contain both W and P, where the Sb can be present in amounts as low as 0.01 atoms Sb per atom of V and (2) a catalyst having the elements and proportions of the co-catalyst herein.

In our copending application Ser. No. 133,661, filed Dec. 16, 1987 is disclosed the ammoxidation of $C_3$ to $C_4$ paraffins, including propane and isobutane, to make nitriles, including acrylonitrile and methacrylonitrile, in the presence of an oxidic V, Sb and W-containing catalyst that can contain P, where the Sb can be present in amounts as low as 0.01 atoms Sb per atom of V.

The following examples of the invention are exemplary and should not be taken as in any way limiting:

EXAMPLE 1

A catalyst having the empirical composition 50 wt % $Bi_4Ce_4Mo_{10}W_2O_x$ + 50 wt % $SiO_2$ was made as follows:

1765.65 g of $(NH_4)_6Mo_7O_{24}\cdot 4H_2O$ were dissolved in 2000 ml warm water. 545.7 g $(NH_4)_6H_2W_{12}O_{40}\cdot H_2O$ - - - 85% $WO_3$ - - - were dissolved with the addition of more $H_2O$, to make a solution of 4750 ml. A 40 wt % $SiO_2$ sol ($NH_4^+$ stabilized) was added in the amount of 8728.75 g.

In a separate beaker, 1940.4 g $Bi(NO_3)_3\cdot 5H_2O$ were dissolved in a mixture of 47.5 ml conc. $HNO_3$ and 250 ml $H_2O$. 2193.04 g $(NH_4)_2Ce(NO_3)_6$ were then dissolved in the solution. The resulting solution was added slowly with stirring to the molybdate tungstate silica solution. The pH of the resulting slurry was adjusted to about 3 by the addition of about 1500 ml of concentrated ammonium hydroxide. A portion of this slurry was then heated and stirred to remove excess water. It was dried overnight at 110° C.

The dried material was denitrified by heating at 290° C. or 3 hours and then at 425° C. for 3 hours. It was ground and screened to between 20-35 mesh particle size. Final calcination was at 650° C. for 3 hours.

EXAMPLE 2

A catalyst having the composition 25% $VPWO_x$-75% $Al_2O_3$ was made. 8.66 g of ammonium metatungstate and 3.75 g of $NH_4VO_3$ were dissolved in 200 cc of hot distilled water and 3.66 g of 85% $H_3PO_4$ was added. Then 8 g of oxalic acid in 50 cc $H_2O$ was added, with stirring for 1 hour at 75° C. Catapal SB alumina (44.12 g) was dispersed in 150 cc $H_2O$ and 7 g acetic acid and stirred vigorously for 1 hour. The resulting sol was then poured slowly to the V-W-P solution. The resulting slurry was slowly evaporated on a hotplate and finally in a 100° C. oven overnight.

The resulting dried precursor was heat-treated at 350° C. for 5 hours, then a portion calcined at 610° C. for 3 hours.

EXAMPLE 3

A catalyst having the composition 50% $VP_{1.2}WO_x$-50% $Al_2O_3$ was made as in Example 2.

EXAMPLE 4

A catalyst having the composition 50% $VP_{1.2}Mn_{0.2}WO_x$-50% $Al_2O_3$ was made in a manner similar to Example 3, except that Mn was added as $Mn(NO_3)_2$.

EXAMPLE 5

A catalyst having the composition 50% $VP_{1.2}O_x$-50% $Al_2O_3$ was made in a manner similar to Example 3, except that no W source was used.

In the ammoxidation runs of the following examples, the catalyst or the catalyst mixture is in a tubular ⅜ inch I.D. stainless steel fixed bed reactor. The reactor is equipped with a preheat leg immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for 0.75 hour to one hour, unless otherwise noted, before the runs are started and product is collected and analyzed: the runs of each example last 30-60 minutes.

In the examples, the conversion, yield and selectivity are defined as follows:

$$\text{conversion} = \frac{\text{moles paraffin reacted}}{\text{moles paraffin charged}} \times 100 \, (\%)$$

$$\text{yield} = \frac{\text{moles product produced}}{\text{moles paraffin charged}} \times 100\ (\%)$$

$$\text{selectivity} = \frac{\text{moles product produced}}{\text{moles paraffin reacted}} \times 100\ (\%)$$

EXAMPLE 6

In this example, the catalyst was the catalyst of Example 2. The reaction temperature was 470° C. and the molar feed ratios were 5 propane/1NH$_3$/2O$_2$/1H$_2$O. The contact time was 0.3 seconds. Analysis of the reactor effluent showed that propane conversion was 20.9 percent; yield and selectivity of propane to acrylonitrile were 2.1 and 10 percent, respectively; yield and selectivity to propylene were 10.6 percent and 50.9 percent, respectively.

EXAMPLE 7

In this example, the catalyst was a mixture of the catalyst of Example 2 and the catalyst of Example 1 in the weight ratio of the former to the latter of 0.035. The reaction temperature was 470° C. and the molar feed ratios were 5 propane/1NH$_3$/2O$_2$/1H$_2$O. The contact time was 2.0 seconds. Analysis of the reactor effluent showed that propane conversion was 9.9 percent; yield and selectivity of propane to acrylonitrile were 4.7 and 47.8 percent, respectively; yield and selectivity to propylene were 0.9 and 8.9 percent, respectively.

EXAMPLE 8

In this example, the catalyst was the catalyst of Example 3. The reaction temperature was 470° C. and the molar feed ratios were 5 propane/1NH$_3$/2O$_2$/1H$_2$O. The contact time was 0.2 seconds. Analysis of the reactor effluent showed that propane conversion was 17.9 percent; yield and selectivity of propane to acrylonitrile were 3.0 and 17.0 percent, respectively; yield and selectivity to propylene were 7.9 percent and 44.1 percent, respectively.

EXAMPLE 9

In this example, the catalyst was a mixture of the catalyst of Example 3 and the catalyst of Example 1 in the weight ratio of the former to the latter of 0.20. The reaction temperature was 470° C. and the molar feed ratios were 5 propane/1NH$_3$/2O$_2$/1H$_2$O. The contact time was 1.9 seconds. Analysis of the reactor effluent showed that propane conversion was 12.7 percent; yield and selectivity of propane to acrylonitrile were 4.2 and 32.8 percent, respectively; yield and selectivity to propylene were 2.1 and 16.7 percent, respectively.

COMPARATIVE EXAMPLE A

In this example, the catalyst was the catalyst of Example 5. The reaction temperature was 470° C. and the molar feed ratios were 5 propane/1NH$_3$/2O$_2$/1H$_2$O. The contact time was 0.2 seconds. Analysis of the reactor effluent showed that propane conversion was 16.7 percent; yield and selectivity of propane to acrylonitrile were 2.4 and 14.2 percent, respectively; yield and selectivity to propylene were 6.8 percent and 40.9 percent, respectively.

EXAMPLE 10

In this example, the catalyst was the catalyst of Example 4. The reaction temperature was 470° C. and the molar feed ratios were 5 propane/1NH$_3$/2O$_2$/1H$_2$O. The contact time was 0.2 seconds. Analysis of the reactor effluent showed that propane conversion was 17.6 percent; yield and selectivity of propane to acrylonitrile were 2.5 and 14.0 percent, respectively; yield and selectivity to propylene were 8.2 percent and 46.4 percent, respectively.

EXAMPLE 11

In this example, the catalyst was a mixture of the catalyst of Example 4 and the catalyst of Example 1 in the weight ratio of the former to the latter of 0.15. The reaction temperature was 470° C. and the molar feed ratios were 5 propane/1NH$_3$/2O$_2$/1H$_2$O. The contact time was 1.9 seconds. Analysis of the reactor effluent showed that propane conversion was 12.7 percent; yield and selectivity of propane to acrylonitrile were 4.8 and 38.0 percent, respectively; yield and selectivity to propylene were 1.5 percent and 11.4 percent, respectively.

As will be evident to those skilled in the art, various modifications of this invention can be made or followed in the light of the foregoing disclosure and discussion without departing from the spirit and scope of the disclosure or from the scope of the claims.

We claim:

1. A complex metal oxide catalyst composition that has 0–99 weight percent of a diluent/support and 100–1 weight percent of a catalyst having the elements and the proportions indicated by the empirical formula:

$$VP_pW_wA_aD_dC_cT_tO_x \qquad \text{(formula 1)}$$

where
- A is one or more of Sn, Mo, B and Ge;
- D is one or more of Fe, Co, Ni, Cr, Pb, Mn, Zn, Se, Te, Ga, Zr, In and As;
- C is one or more of an alkali metal and Tl;
- T is one or more of Ca, Sr, Mg and Ba; and
- where a is 0–10; d is 0–10; c is 0–1; t is 0–10; p is 0.1–20; w is 0.2–10; the ratio (a+c+d+t+w):(1+p) is no more than 6; and no more than 2 atoms of Mo are present per atom of V, which catalyst composition is in particulate form and is admixed with a co-catalyst composition also in particulate form and having 0–99 weight percent of a diluent/support and 100–1 weight percent of a co-catalyst having the elements and the proportions indicated by the empirical formula:

$$Bi_nCe_pD_dE_eF_fMo_{12}W_gO_y \qquad \text{(formula 2)}$$

where
- D is one or more of Fe, Mn, Pb, Co, Ni, Cu, Sn, P, Cr, Y, Mg, Ca, Sr, Ba and rare earths other than Ce and Sm
- E is one or more of Sb, Ge, As, Se, Te and V
- F is one or more of an alkali metal, Tl, Ag and Sm
and where n is 0.01–24, p is 0.01–24, (n+p) is 0.1–24, d is 0–10, e is 0–10, f is 0–6, g is 0–8, y is determined by the oxidation state of other elements, wherein the weight ratio of said catalyst composition to said co-catalyst composition is in the range of 0.001 to 2.5.

2. A particulate mixture in accordance with claim 1 wherein said catalyst contains at least 0.4 atom of W per atom of V.

3. A particulate mixture in accordance with claim 1 wherein said catalyst contains at least 0.5 atom of P per atom of V.

4. A particulate mixture in accordance with claim 3 wherein said catalyst contains at least 0.4 atom of W per atom of V.

* * * * *